United States Patent [19]

Bates

[11] Patent Number: 4,460,362
[45] Date of Patent: Jul. 17, 1984

[54] DRAINAGE SYSTEM WITH HOLDING CHAMBER

[75] Inventor: David A. Bates, Libertyville, Ill.

[73] Assignee: The Kendall Company, Boston, Mass.

[21] Appl. No.: 400,518

[22] Filed: Jul. 21, 1982

[51] Int. Cl.³ ............................................. A61M 1/00
[52] U.S. Cl. .................................... 604/323; 604/335
[58] Field of Search ........ 604/335, 350, 317, 322–326;
128/DIG. 24, 760, 762, 765, 766, 767, 768;
417/520, 571; 137/99, 240, 572; 251/9;
222/428, 429, 452

[56] References Cited

U.S. PATENT DOCUMENTS

| | | | |
|---|---|---|---|
| 3,780,757 | 12/1973 | Jordan | 137/209 |
| 3,904,326 | 9/1975 | Clement | 417/571 |
| 3,906,935 | 9/1975 | Raia et al. | 604/323 |
| 4,246,932 | 1/1981 | Raines | 604/30 |
| 4,386,930 | 6/1983 | Cianci | 604/317 |

Primary Examiner—C. Fred Rosenbaum
Assistant Examiner—J. L. Kruter
Attorney, Agent, or Firm—Powell L. Sprunger

[57] ABSTRACT

A drainage system for body fluids comprising, a receptacle having a collection chamber for retaining the body fluids, a container having a supply chamber for retaining a bactericide, and a holding chamber. The system has a first one-way valve member permitting the passage of bactericide from the supply chamber into the holding chamber, and preventing passage of the bactericide from the holding chamber into the supply chamber. The system has a second one-way valve member for permitting passage of the bactericide from the holding chamber into the collection chamber, and for preventing passage of the contents from the collection chamber into the holding chamber.

11 Claims, 7 Drawing Figures

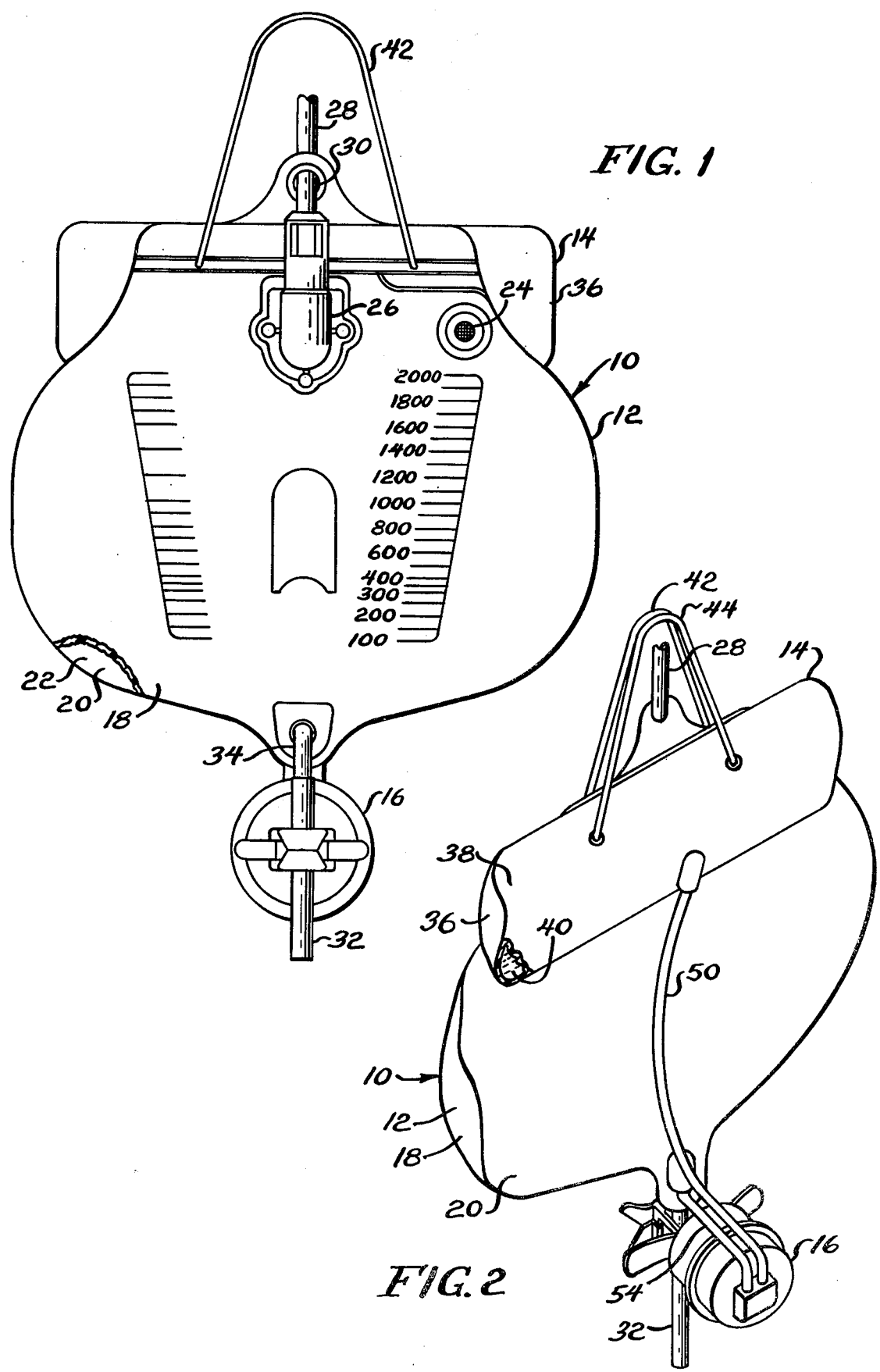

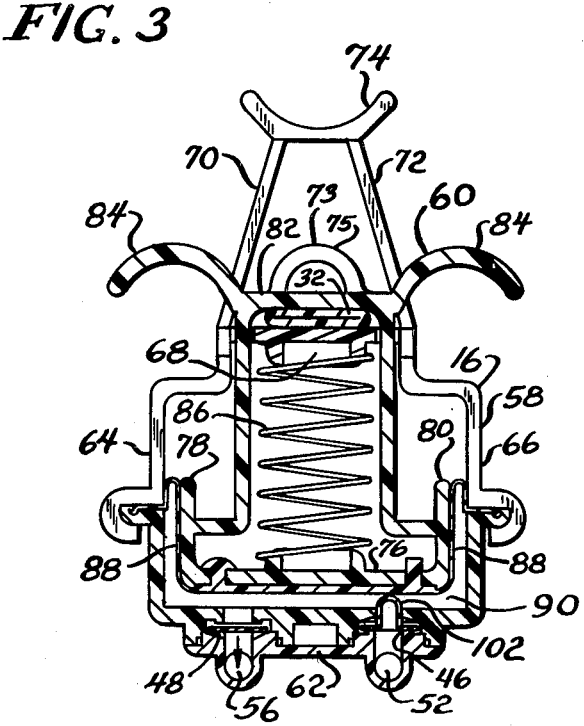
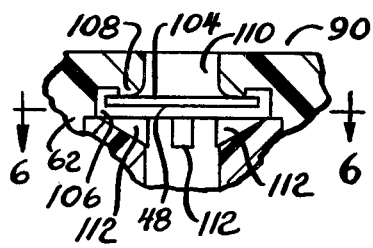
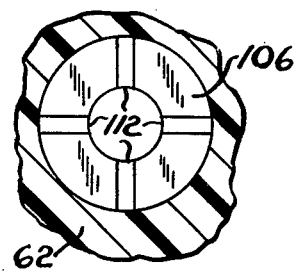
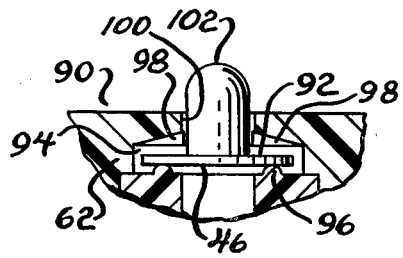
FIG. 3
FIG. 4
FIG. 5
FIG. 6
FIG. 7

DRAINAGE SYSTEM WITH HOLDING CHAMBER

BACKGROUND OF THE INVENTION

The present invention relates to drainage systems for urine.

Urine drainage systems of the type comprising a catheter and collection receptacle are known. In such systems, a distal end of the catheter is passed through the urethra of a patient until it is located in the bladder, with a proximal end of the catheter being located outside the patient's body. An upstream end of a drainage tube is connected to the proximal end of the catheter, and a downstream end of the drainage tube communicates with a collection chamber in the receptacle. In use, urine drains through a drainage eye in the distal end of the catheter, and through the catheter and drainage tube into the collection chamber for retention therein.

Since such systems are closed to the atmosphere, contamination of the systems is minimized. However, it has been found that bacteria may grow in the collected urine in the receptacle, and may move in retrograde fashion to the patient's bladder resulting in possible harm to the patient. It has been attempted to introduce a bactericide into the collection chamber at periodic intervals, and the bactericide minimizes the possibility of bacteria growth in order to solve this problem. However, in prior devices separate loose containers of the bactericide are required, resulting in retention of extra parts and inconvenience to hospital personnel. Also, the bactericide has been introduced through a slit in a rubber plug which poses a risk of contamination in the receptacle.

SUMMARY OF THE INVENTION

A principal feature of the present invention is the provision of an improved drainage system of simplified construction.

The drainage system of the invention comprises, a receptacle having a collection chamber for retaining body fluids, and a drainage tubular section of flexible material communicating with the collection chamber. The system has a container having a supply chamber for retaining a bactericide. The system also has a clamping apparatus comprising a first clamp member and a second clamp member with the tubular section being received between portions of the first and second clamp members. The clamping apparatus includes a flexible diaphragm connected between the first and second clamp members and defining a holding chamber with the first and second clamp members. The first and second clamp members are movable between a first position with the portions being spaced and the diaphragm flexed to an expanded condition of the holding chamber, and a second position with the portions engaging against the tubular section and the diaphragm flexed to a contracted condition of the holding chamber. The system has means for biasing the clamping apparatus from the first to second position. The system has first one-way valve means, and second one-way valve means.

A feature of the present invention is that the tubular section is substantially open to permit drainage of liquid from the receptacle at the first position of the first and second clamp members.

Another feature of the invention is that the tubular section is closed to prevent passage of liquid through the tubular section at the second position of the first and second clamp members.

Yet another feature of the invention is that the first one-way valve means opens to permit passage of the bactericide from the supply chamber into the holding chamber responsive to movement of the clamping apparatus to the first position.

Still another feature of the invention is that the first one-way valve means closes to prevent passage of the bactericide from the holding chamber into the supply chamber responsive to movement of the clamping apparatus to the second position.

Yet another feature of the invention is that the second one-way valve means opens to permit passage of the bactericide from the holding chamber into the collection chamber responsive to movement of the clamping apparatus to the second position A further feature of the invention is that the second one-way valve means closes to prevent passage of the contents of the collection chamber into the holding chamber responsive to movement of the clamping apparatus to said first position.

Thus, a feature of the present invention is that a quantity of the bactericide is automatically injected into the collection chamber when the contents of the receptacle is emptied through the tubular section.

Further features will become more fully apparent in the following description of the embodiments of this invention and from the appended claims.

DESCRIPTION OF THE DRAWINGS

In the drawings:

FIG. 1 is a fragmentary front elevational view of a drainage system of the present invention;

FIG. 2 is a fragmentary rear perspective view of the drainage system of FIG. 1;

FIG. 3 is a sectional view of clamping apparatus in the drainage system in a position with a tubular section of a receptacle closed;

FIG. 4 is a sectional view of the clamping apparatus in the drainage system in a position with the tubular section open;

FIG. 5 is a fragmentary sectional view of a one-way valve member in the clamping apparatus;

FIG. 6 is a fragmentary sectional view taken substantially as indicated along the line 6—6 of FIG. 5; and FIG. 7 is a fragmentary sectional view of another one-way valve member in the clamping apparatus.

DESCRIPTION OF THE PREFERRED EMBODIMENTS

Referring now to FIGS. 1 and 2, there is shown a urinary drainage system generally designated 10 having a receptacle 12, a container 14, and clamping apparatus 16. The receptacle 12 has front and back walls 18 and 20 of suitable flexible plastic material joined at their periphery to define a collection chamber 22 between the front and back walls 18 and 20. The receptacle 12 may have a vent 24 communicating between the chamber 22 and the atmosphere with a bacteria filter to prevent passage of bacteria into the chamber 22. The receptacle 12 has a connector 26 in the form of a drip chamber attached to an upper portion of the front wall 18 and communicating with the chamber 22. The system 10 has an elongated drainage tube 28 having a downstream end 30 attached to the connector 26, such that the drainage tube 28 communicates with the collection chamber 22 through the connector 26. The receptacle 12 also has a tubular section 32 of flexible elastic material having an inner end 34 attached to a lower portion of the front wall 18, such that the tubular section 32 communicates with the collection chamber 22.

In use, a distal end of a catheter (not shown) is inserted through the urethra of a patient until the distal end of the catheter is located in the patient's bladder, with a proximal end of the catheter located outside the patient's body. An upstream end of the drainage tube 28 is connected to the proximal end of the catheter. Urine drains through a drainage eye in the distal end of the catheter, through the catheter and drainage tube 28 into the collection chamber 22 for retention therein. It has been found that bacteria has tendency to grow in the environment of the collected urine in the collection chamber 22, and may pass by retrograde movement through the drainage tube 28 and catheter into the patient's bladder with possible harmful results to the patient. The present invention is directed to a device to minimize the possibility of bacteria growth in the collection chamber 22.

The container 14 has a front wall 36 and a back wall 38 joined at their periphery to define a supply chamber 40 to retain a supply of a liquid bactericide, such as chlorhexidine gluconate. As shown, the container 14 is located adjacent the upper rear portion of the receptacle 12, and the receptacle 12 and container 14 may be supported from a suitable object, such as a bed rail, by a pair of cords 42 and 44. With reference to FIGS. 3 and 4, the clamping apparatus 16 has a first one-way valve member 46, and a second one-way valve member 48. With reference to FIGS. 1-3, the system 10 has a first conduit 50 communicating between a lower portion of the supply chamber 40 of the container 14 and an opening 52 of the clamping apparatus 16, such that the first conduit 50 communicates between the container 14 and the first valve member 46. The system 10 also has a second conduit 54 communicating between an opening 56 associated with the second valve member 48 and a lower portion of the collection chamber 22 of the receptacle 12, such that the second conduit 54 communicates between the second valve member 48 and the receptacle 12.

The clamping apparatus 16 is shown in detail in FIGS. 3 and 4. The clamping apparatus 16 comprises a first clamp member 58 and a second clamp member 60 which are movable with respect to each other. The first clamp member 58 has a first wall 62 housing the first and second valve members 46 and 48, and a pair of sidewalls 64 and 66 extending from opposed ends of the first wall 62. The first clamp member 58 has a clamping portion 68 extending between ends of the sidewalls 64 and 66, and being spaced from the first wall 62. The first clamp member 58 also has a pair of arms 70 and 72 extending outwardly from the clamping portion 68. The first clamp member 58 has a gripping flange 74 connected to the outer ends of the arms 70 and 72. The first clamp member 58 has a retaining bar 73 extending between the arms 70 and 72 and having a semi-circular retaining portion 75 in a center of the bar 73.

The second clamp member 60 has a first wall 76 facing the first wall 62 of the first clamp member 58. The second clamp member 60 has a pair of opposed sidewalls 78 and 80 extending from opposed ends of the first wall 76, and a clamping portion 82 extending between outer ends of the sidewalls 78 and 80. As shown, the second clamp member 60 has a pair of gripping flanges 84 extending from opposed ends of the clamping portion 82.

The tubular section 32 is received between the clamping portions 68 and 82 of the first and second clamp members 58 and 60, respectively. The clamping apparatus 16 has a helical spring 86 extending between the clamping portion 68 of the first clamp member 58 and the first wall 76 of the second clamp member 60, such that the spring 86 is connected between the first and second clamp members 58 and 60. The clamping apparatus 16 has a flexible diaphragm 88 connected and extending between the sidewalls 64 and 66 of the first clamp member 58 and the sidewalls 78 and 80 of the second clamp member 60. Thus, the diaphragm 88, sidewalls 64 and 66 of the first clamp member 58, first wall 62 of the first clamp member 58, and the first wall 76 of the second clamp member 60 define a holding chamber 90, with the holding chamber 90 communicating with the first and second valve members 46 and 48.

With reference to FIGS. 3 and 7, the first valve member 46 comprises a disc 92 received in a cavity 94 in the first wall 62 of the first clamp member 58. The first wall 62 has an annular seat 96, such that the first valve member 46 prevents passage of liquid between the holding chamber 90 and the opening 52 when the disc 92 is engaged against the seat 96 at a first position of the valve member 46. However, when the disc 92 moves to a second position spaced from the seat 96, liquid is permitted to pass from the opening 52 around the disc 92, through a plurality of apertures 98, and through an opening 100 into the holding chamber 90. Thus, the first one-way valve member 46 permits passage of liquid from the container 14 through the first valve member 46 into the holding chamber 90, but prevents passage of liquid from the holding chamber 90 past the first one-way valve member 46 into the container 14. As shown, the disc 92 has a boss 102 extending through the opening 100 into the holding chamber 90 for a purpose which will be described below.

With reference to FIGS. 3, 5, and 6, the second valve member 48 has a disc 104 received in a cavity 106 in the first wall 62. The first wall 62 of the first clamp member 58 has an annular valve seat 108 extending around an opening 110 communicating with the holding chamber 90. When the disc 104 is engaged against the seat 108, the second valve member 48 prevents passage of liquid from the opening 56 to the holding chamber 90. However, when the disc 104 is spaced from the seat 108, liquid is permitted to pass from the holding chamber 90 around the disc 104 and through a plurality of apertures 112 into the opening 56. Thus, the second one-way valve member 48 permits passage of liquid from the holding chamber 90 into the collection chamber 22 of the receptacle 12, but prevents passage of liquid contents from the collection chamber 22 of the receptacle 12 into the holding chamber 90.

The clamping apparatus 16 is movable between a first position, as shown in FIG. 4, and a second position, as shown in FIG. 3, with the gripping flanges 74 and 84 facilitating manipulation of the first and second clamp members 58 and 60 between the first and second positions. As shown in FIG. 4, in the first position of the clamping apparatus 16 the clamping portions 68 and 82 of the first and second clamp members 58 and 60, respectively, are spaced from each other in order to open the tubular section 32 to permit drainage of urine from the collection chamber 22 through the tubular section 32, with the tubular section 32 being held in place by the retaining portion 75 of the bar 73. In the first position of the clamping apparatus 16, the diaphragm 88 is flexed to an enlarged configuration of the holding chamber 90 to expand the holding chamber 90 and create suction in the holding chamber 90. In response to movement of the clamping apparatus 16 to the first position, the first valve member 46 opens to permit passage of a quantity of the bactericide from the container 14 through the first valve member 46 into the holding chamber 90. Also, in response to movement of the clamping apparatus 16 to the first position, the suction in the holding chamber 90 causes the second valve member 48 to close, thus preventing passage of the contents of the collection chamber 22 into the holding chamber 90. Thus, when the clamping apparatus 16 is moved to the first position, the tubular section 32 is open to drain urine from the collection chamber 22, and the first valve member 46 is opened to cause passage of bactericide into the holding chamber 90 from the container 14.

The clamping apparatus 16 is movable to the second position, as shown in FIG. 3. In this configuration, the clamping portions 68 and 82 of the first and second clamp members 58 and 60 engage against the tubular section 32 and close the tubular section 32 to prevent passage of liquid from the collection chamber 22 through the tubular section 32. Also, in this configuration, the diaphragm 88 is flexed to a contracted condition of the holding chamber 90 to cause pressure in the holding chamber 90. In response to movement of the clamping apparatus 16 to the second position, the second valve element 48 is opened to permit passage of the bactericide from the holding chamber 90 into the collection chamber 22 of the receptacle 12. Also, in response to movement of the clamping apparatus 16 to the second position, the first valve member 46 is closed to prevent passage of bactericide from the holding chamber 90 back into the container 14. As shown, the first wall 76 of the second clamp member 60 engages against the boss 102 of the first valve member 46 in order to maintain the disc 92 engaged against the seat 96, thus maintaining the first valve member 46 in a closed condition in order to prevent passage of liquid from the container 14 into the holding chamber 90. It will be apparent with reference to FIGS. 3 and 4 that the spring 86 biases the clamping apparatus 16 from the first position as shown in FIG. 4, to the second position as shown in FIG. 3, such that the clamping apparatus 16 automatically moves between the first to second position.

In use, the patient is catheterized, and urine is permitted to collect over a period of time in the collection chamber 22. When it is desired to empty the contents of the collection chamber 22, the gripping elements 74 and 84 are manipulated to move the clamping apparatus 16 from the second position shown in FIG. 3 to the first position shown in FIG. 4 at which time the tubular section 32 is opened to permit drainage of urine through the tubular section 32. Also, at this time, the first valve member 46 is opened to permit passage of the bactericide from the container 14 into the holding chamber 90, while the second valve member 48 is closed to prevent passage of the contents of the collection chamber 22 into the holding chamber 90. When drainage of the collection chamber 22 has been completed, the gripping flanges 74 and 84 are released, and the spring 86 biases the clamping apparatus 16 to the second position, as shown in FIG. 3, in order to close the tubular section 32. Also at this time, the first valve member 46 is closed, and the second valve member 48 is opened to permit passage of the bactericide from the holding chamber 90 into the collection chamber 22. Thus, in accordance with the present invention, a quantity of the bactericide is automatically introduced from the container 14 into the receptacle 12 responsive to emptying of the collection chamber 22, and the bactericide introduced into the collection chamber 22 at the start of each collection period minimizes the possibility of bacteria growth in the collection chamber 22.

The foregoing detailed description is given for clearness of understanding only, and no unnecessary limitations should be understood therefrom, as modifications will be obvious to those skilled in the art.

I claim:

1. A drainage system for body fluids, comprising:
   a receptacle having a collection chamber for retaining the body fluids;
   a container having a supply chamber;
   a bactericide in the supply chamber;
   means defining a holding chamber;
   first one-way valve means permitting the passage of bactericide from the supply chamber into the holding chamber, and for preventing passage of the bactericide from the holding chamber into the supply chamber; and
   second one-way valve means for permitting passage of the bactericide from the holding chamber into the collection chamber, and for preventing passage of the contents from the collection chamber into the holding chamber, wherein the receptacle includes a drainage tubular section of flexible material, and including clamp means for opening the tubular section while the first valve means is open, and for closing the tubular section while the second valve means is open.

2. The system of claim 1 including means for opening the first valve means while closing the second valve means, and means for opening the second valve means while closing the first valve means.

3. The system of claim 1 including means for maintaining the first valve means closed while the tubular section is closed.

4. The system of claim 1 including a first conduit communicating between the supply chamber and the first valve means, and a second conduit communicating between the second valve means and the collection chamber.

5. A drainage system for body fluids, comprising:
   a receptacle having a collection chamber for retaining the body fluids, and a drainage tubular section of flexible material communicating with the collection chamber;
   a container having a supply chamber for retaining a bactericide;
   clamp means defining a holding chamber and movable between a first position with the tubular section open and the holding chamber in an expanded condition, and a second position with the tubular section closed and the holding chamber in a contracted condition;
   first one-way valve means opening to permit passage of the bactericide from the supply chamber into the holding chamber responsive to movement of the clamp means to said first position, and closing to prevent passage of the bactericide from the holding chamber to the supply chamber responsive to movement of the clamp means to said second position; and second one-way valve means opening to permit passage of the bactericide from the holding chamber into the collection chamber responsive to movement of the clamp means to said second position, and closing to prevent passage of the contents of the collection chamber into the holding chamber responsive to movement of the clamp means to said first position.

6. A drainage system for body fluids, comprising:
a receptacle having a collection chamber for retaining the body fluids, and a drainage tubular section of flexible material communicating with the collection chamber;
a container having a supply chamber for retaining a bactericide;
a clamping apparatus comprising a first clamp member and a second clamp member with the tubular section being received between portions of the first and second clamp members, said clamping apparatus including a flexible diaphragm connected between the first and second clamp members and defining a holding chamber with the first and second clamp members, said first and second clamp members being movable between a first position with said portions being spaced sufficiently such that the tubular section is substantially open, and said diaphragm is flexed to an expanded condition of the holding chamber, and a second position with said portions engaging against the tubular section such that the tubular section is closed, and said diaphragm is flexed to a contracted condition of the holding chamber;
means for biasing the clamping apparatus from said first to second position;
first one-way valve means opening to permit passage of the bactericide from the supply chamber into the holding chamber responsive to movement of the clamping apparatus to said first position, and closing to prevent passage of the bactericide from the holding chamber into the supply chamber responsive to movement of the clamping apparatus to said second position; and
second one-way valve means opening to permit passage of the bactericide from the holding chamber into the collection chamber responsive to movement of the clamping apparatus to said second position, and closing to prevent passage of the contents of the collection chamber into the holding chamber responsive to movement of the clamping apparatus to said first position.

7. The system of claim 6 including a first conduit communicating between the supply chamber and the first valve means, and a second conduit communicating between the second valve means and the collection chamber.

8. The system of claim 6 wherein the biasing means comprises a helical spring connected between the first and second clamp members.

9. The system of claim 6 wherein the first and second clamp members include gripping flanges to facilitate manipulation of the clamping apparatus between said first and second position.

10. The system of claim 9 wherein said first valve means comprises a disc valve having a boss extending into the holding chamber, and in which the clamping apparatus engages against said boss at said second position to maintain said valve closed.

11. A drainage system for body fluids, comprising:
a receptacle having a collection chamber for retaining the body fluids;
a container having a supply chamber;
a bactericide in the supply chamber;
means defining a holding chamber;
first one-way valve means permitting the passage of bactericide from the supply chamber into the holding chamber, and for preventing passage of the bactericide from the holding chamber into the supply chamber;
second one-way valve means for permitting passage of the bactericide from the holding chamber into the collection chamber, and for preventing passage of the contents from the collection chamber into the holding chamber; and
means for expanding the holding chamber and for opening the first valve means while closing the second valve means, and means for contracting the holding chamber and for opening the second valve means while closing the first valve means, wherein the receptacle includes a drainage tubular section of flexible material, and including clamp means for opening the tubular section during expansion of the holding chamber, and for closing the tubular section during contraction of the tubular section.

* * * * *